(12) United States Patent
Davies et al.

(10) Patent No.: US 6,224,760 B1
(45) Date of Patent: *May 1, 2001

(54) CHROMATOGRAPHY COLUMN END ARRANGEMENTS

(76) Inventors: John Davies, 65 Insley Gardens, Hucclecote, Gloucestershire, GL3 3AU; Gerald James Spencer, 14 Chacley Street, Abbeymead, Gloucestershire, GL4 4XP, both of (GB); Owe Persson, Måskensvägen 20D, 743 35 Storvreta (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/092,239

(22) Filed: Jun. 5, 1998

(30) Foreign Application Priority Data

Jun. 6, 1997 (SE) .................................................. 9702169

(51) Int. Cl.$^7$ .................................................. B01D 15/08
(52) U.S. Cl. ................ 210/198.2; 210/456; 210/656; 96/107
(58) Field of Search .................. 210/635, 656, 210/659, 198.2, 198.3, 456; 96/107

(56) References Cited

U.S. PATENT DOCUMENTS

| | | | |
|---|---|---|---|
| 4,557,830 | * 12/1985 | Onitsuka .......................... | 210/198.2 |
| 4,582,608 | 4/1986 | Ritacco ............................ | 210/198.2 |
| 4,891,133 | 1/1990 | Colvin, Jr. ........................ | 210/198.2 |
| 4,894,152 | 1/1990 | Colvin, Jr. et al. ................ | 210/198.2 |
| 5,013,433 | 5/1991 | Shalon ............................. | 210/198.2 |
| 5,116,443 | * 5/1992 | Meurer ............................. | 210/521 |
| 5,141,635 | * 8/1992 | Le Planz .......................... | 210/198.2 |
| 5,167,809 | * 12/1992 | Mann .............................. | 210/198.2 |
| 5,167,810 | * 12/1992 | Vassarotti ........................ | 210/198.2 |
| 5,238,556 | * 8/1993 | Shirkham ......................... | 210/198.2 |
| 5,324,426 | 6/1994 | Joseph et al. .................... | 210/198.2 |
| 5,423,982 | * 6/1995 | Jungbauer ........................ | 210/198.2 |
| 5,601,708 | * 2/1997 | Leavesley ........................ | 210/198.2 |
| 5,863,428 | * 1/1999 | Ma ................................. | 210/198.2 |
| 5,985,140 | * 11/1999 | Dewaele .......................... | 210/198.2 |

FOREIGN PATENT DOCUMENTS

| | | |
|---|---|---|
| 2085614 | 4/1982 | (GB) . |
| 2110951 | 6/1983 | (GB) . |
| WO 96/10451 | 4/1996 | (WO) . |
| WO 96/26436 | 8/1996 | (WO) . |

\* cited by examiner

*Primary Examiner*—Ernest G. Therkorn
(74) *Attorney, Agent, or Firm*—Royal N. Ronning, Jr.

(57) ABSTRACT

A chromatography column having an end arrangement including an end plate having a fluid opening and a filter extending over an internal surface of the end plate to define a fluid flow zone between them into which the fluid flow opens is disclosed. There is a liner between the end plate's internal surface and the filter layer. The liner has a surface relief pattern to space the filter layer from the end plate and maintain the fluid flow zone across the filter.

9 Claims, 3 Drawing Sheets

CHROMATOGRAPHY COLUMN END ARRANGEMENTS

The invention relates co apparatus for the separation of substances by chromatography, in particular to the end constructions of chromatography columns.

Chromatography is widely used for the separation of substances held in fluid media. A typical column has an upright housing filled in use with packing material. The packing material is retained in the column by end arrangements, each having an end plate, fluid inlet/outlet opening(s) communicating through the end plate to an internal flow surface thereof, and a filter layer covering the internal flow surface. The end plate may be axially movable relative to the column housing.

The filter layer allows fluid medium to pass over the cross-section of the column while retaining the packing material.

The end plate's internal flow surface is typically recessed towards the centre of the plate e.g. as a generally conical surface, with one or more central through-passages for the fluid inlet/outlet. The recessed end plate surface provides the rear surface of a flow zone which is defined between the end plate and the filter layer and is of importance in ensuring distribution of flow over the filter's flow area: without uniform flow there can be no satisfactory chromatography. To this end the conventional end plate flow surface has a centrosymmetric array of upstanding radial ribs. These also support the rear surface of the filter layer to maintain the flow zone and protect the filter layer against flow forces and packing weight. The maxima of the ribs may themselves provide a conical contour so that the installed filter layer takes a conical form.

The filter layer itself is typically a disc, secured against the end plate around its outer edge and usually also at its centre which may have a central opening for a packing nozzle, e.g. as disclosed in our WO-A-96/10451.

The conventional manufacture of a ribbed end plate is by machining, followed by laborious grinding, polishing and electropolishing steps to get the, desired smoothness of finish. A smooth finish is important in chromatography because the smoother the finish, the more uniform the flow and (especially important in the pharmaceutical field) the less the likelihood of contamination. With plastics end plates the best obtainable smoothness is only that which can be got by careful machining.

What we now propose is to provide a liner layer between the end plate and the surface layer, the liner layer having an obverse surface which provides a rear surface for the flow zone and is formed with a surface relief pattern to support the filter layer from behind and/or direct flow distribution in the flow zone.

Because a relatively thin liner layer need not serve the structural function of the relatively thick end plate its use brings substantial manufacturing flexibility Furthermore a particular preference is to shape the liner from prefabricated uniform sheet material, e.g. metal or plastics sheet, creating the surface relief pattern by permanent deformation of the sheet material. This can be done against a shaped former e.g. urging the sheet by pressing or vacuum-forming, so as to produce reliefs on one side corresponding to recesses on the other.

An excellent surface finish may then be achieved by comparison with conventional machining, because sheet materials are routinely available with a high degree of surface smoothness which can be substantially retained when the relief pattern is formed. This is particularly advantageous for plastics components, which are not susceptible to smoothing after machining.

It is possible to make the liner layer by other methods such as casting or moulding. These can give a surface finish better than machining but usually less good than by deforming sheet material as mentioned above. All of these techniques however provide an excellent alternative to making and finishing surface reliefs on the structural end plate itself.

The liner may be formed in one piece or as a plurality of segments according to choice; a one-piece liner is simpler to install but a segmented liner can be made with smaller forming apparatus; significant when the end plate is larger.

The surface relief pattern preferably defines a set, of channels extending side-by-side away from an opening for fluid medium. Note that this "opening" may be a set of openings. An array of ribs is suitable. The usual arrangement has a circular liner with one or more central openings for fluid medium and an array of elongate ribs extending wholly or partly radially. The favoured arrangement, as on conventional machined end plates, has a set of major radial ribs—extending substantially from the inner to the outer periphery of the flow zone—and one or more sets of minor radial ribs positioned between the main ribs towards the outer periphery to sub-divide what would otherwise be larger rib spacing in that region.

The liner's obverse reliefs may provide mechanical support for the filter layer, in that the filter layer lies against them and desirably is fixed to them. The maxima of the relief pattern may define a flat or conically recessed support contour against which the filter layer lies to assume a corresponding form.

The reverse of the liner lies against an internal surface of the end plate. For purposes of mechanical support it is preferred that these surfaces are substantially complementary. Usually at least the inner and outer peripheries and preferably also those zones not corresponding to the shaped reliefs are formed to complement the end plate's internal surface. The end plate's internal surface is preferably recessed with a generally conical internal form, and provided with an opening (usually a central opening or centrosymmetric arrangement of central openings) for the passage of fluid medium. Since relief patterning and surface finish are provided by the liner, the end plate's internal surface can be plain. For additional mechanical support, however, it is possible to machine the end plate with reliefs corresponding to all or some of those of the liner and fitting into recesses on the liner's reverse. Benefit is still obtained because the liner cad provide an excellent surface finish and the machined end plate surfaces do not need to be finished.

The liner is preferably an impermeable arrangement secured to the end plate with its reverse side sealed from the flow zone. For this purpose the liner (or its segments) can have a continuous reverse surface region e.g. a perimeter margin region, which complements the end plate internal surface and is sealed to it e.g. by welding or clamping.

The filter layer itself may be conventional. Either metal or plastics filter layers can be used, usually selecting a material corresponding to that of the adjacent parts of the apparatus, and may be fitted onto or adjacent the liner by means well-known to a skilled person, e.g. welding or clamping.

The liner and filter may be assembled together to form an integrated fuzer-liner unit before fitting this onto the end plate. By combining these two components before final assembly, on-site operations can be simplified.

The end plate may have one or more through-channels to the region between the liner and end plate, for leak testing a seal between them e.g. by applying gas pressure.

BRIEF DESCRIPTION OF THE DRAWINGS

Embodiments of our proposals are now described by way of example, with reference to the accompanying drawings in which.

DESCRIPTION OF THE PREFERRED EMBODIMENTS

Figure 4:
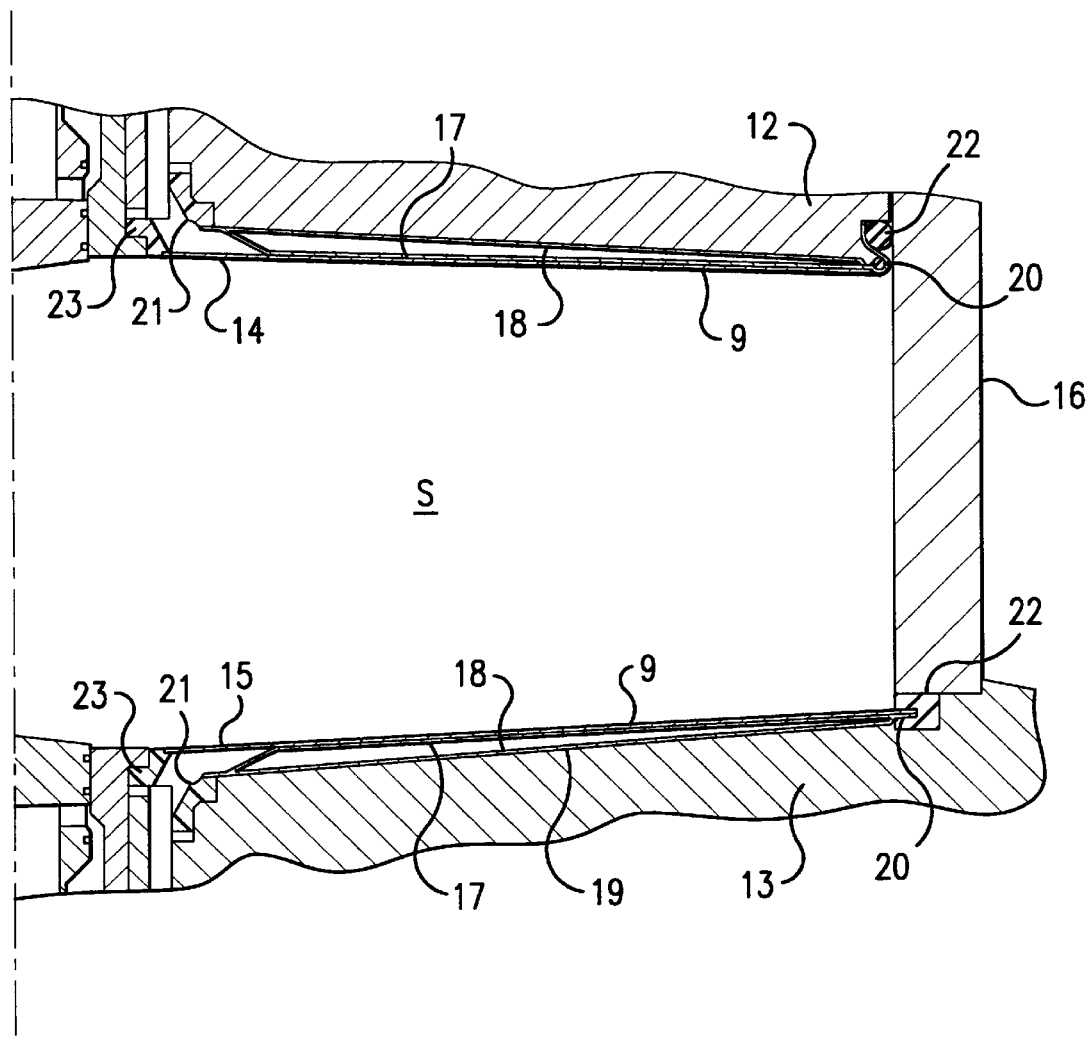
FIG. 4 is a half cross-section showing upper and lower end plate arrangements and part of a column housing.

The construction shown in FIG. 4 is specifically adapted for manufacture in plastics material, e.g. with polypropylene end plates, but the general principles apply to the use of other materials as well.

A cylindrical bed space S is defined by a cylindrical housing wall 16 and circular upper and lower end plates 12,13. In this version the annular foot of the housing wall 16 seats fixedly against the lower end plate 13, while the upper end plate 12 is axially movable piston-fashion within the housing wall 16 by virtue of a peripheral sliding seal 22. Each end plate 12,13 has a series of central fluid-flow openings 21 for the passage of fluid medium in chromatography. One or both of the end plates may also be fitted with a valve or other suitable means for packing and/or unpacking solid medium to/from the bed space S; this is known as such and not directly associated with the present concepts.

Around the central flow opening(s) 21 the end plates 12,13 have internal surfaces 19 formed as a smooth, shallow cone. Unlike a conventional end plate interior this conical surface 19 is a plain one, i.e free of surface ribbing. A discrete liner disc 9 is fitted against it, providing an array of raised projections 17 which support a filter layer 14,15 from behind. The filter layers 14,15 may be generally conventional, having a central opening which corresponds to the central installation of the end plate and whose periphery is secured around that installation. The outer peripheries of the filter layers also held in place against the respective end plates 12,13 by means discussed in more detail later; again this may be in itself conventional.

The use of the liners 9 is a special feature of the arrangement. Details of these will be better understood by referring also to FIGS. 1 to 3. Certain specifics in these figures are concerned with metal rather than plastics liners, but the general features now described are applicable to FIG. 4.

Figure 2:
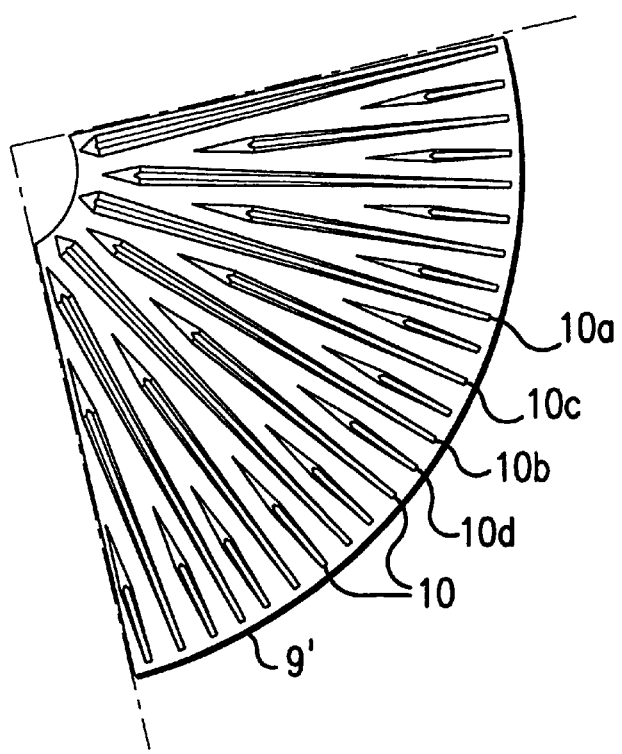
FIG. 2 is an obverse plan view of a liner segment.
Figure 3:
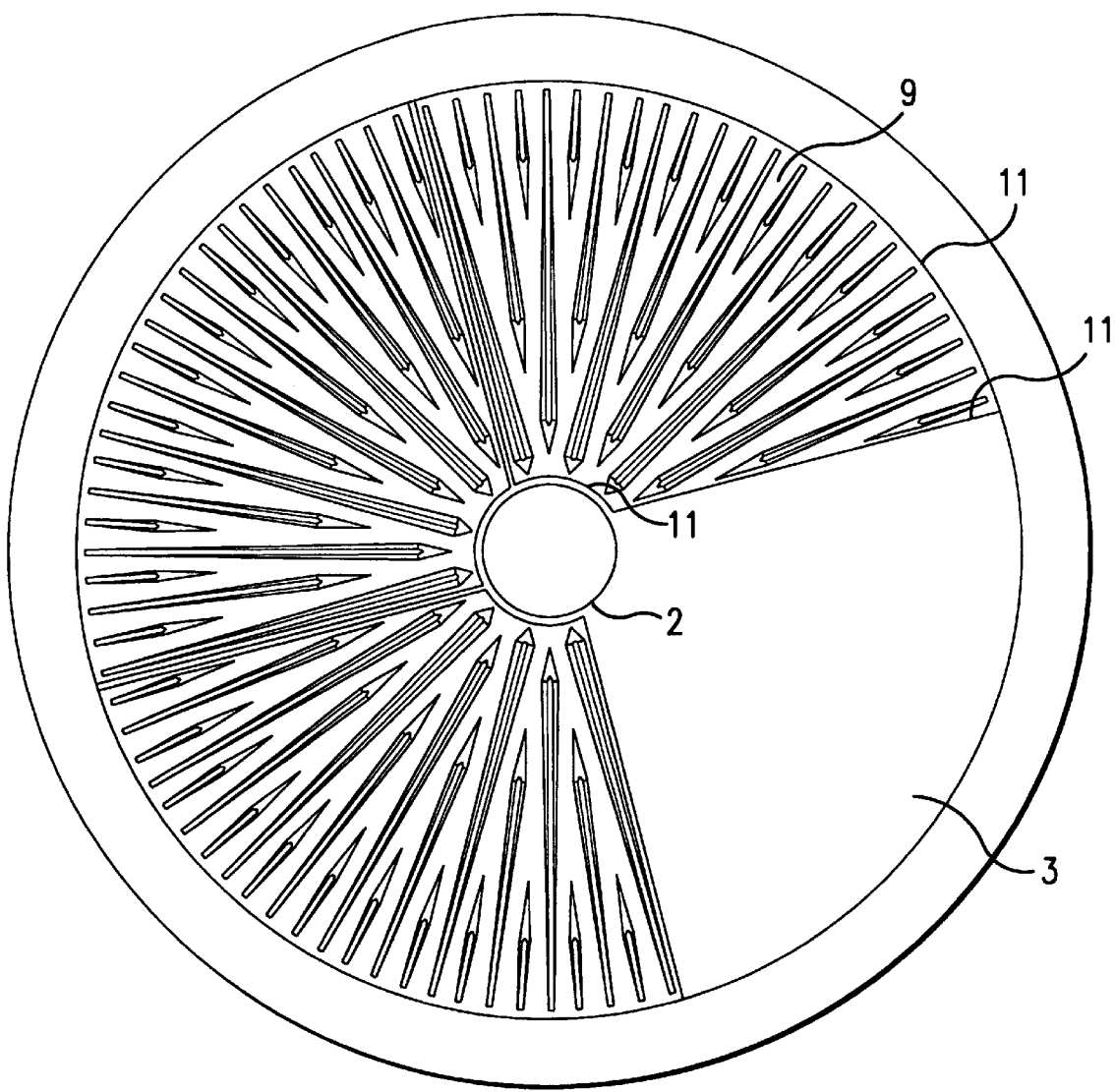
FIG. 3 is an obverse plan view of three liner segments on the end plate of FIG. 2.

The liner 9 is made from sheet material shaped (as described below) so that the sheet 18 as a whole takes on a conical form corresponding to the conical surface 19 of the end plate. The sheet material is also shaped to provide the above-mentioned projections 17, which as seen in FIGS. 2 and 3 take the form of an array of angularly spaced radial ribs 10. Major ribs 10a extend substantially from the inner to the outer edge of the liner 9 while shorter sets of ribs 10b,10c,10d are distributed between these, progressively away from the centre, to maintain the level of occupation of the flow zone by rib projections and therefore maintain a generally uniform support behind the filter layer 14,15. In use, fluid medium is guided along the channels between the ribs to distribute flow evenly around the end plate. The pattern of ribs as such is not critical, and may correspond to patterns already known for machining into an end plate.

FIGS. 2 and 3 show a liner made up of four liner segments or sectors 9' each of 90° extent. The use of segments is a matter of manufacturing convenience, especially with larger columns whose diameter may be over 2 metres and for which it would be difficult to create a one-piece liner. One might use up to 10 or more segments for a large column, whereas for a small column it may be convenient to make the liner in one piece.

Figure 1:
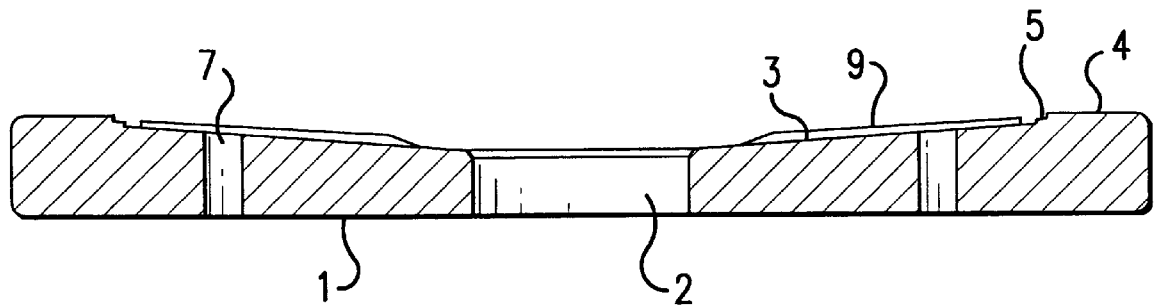
FIG. 1 is a radial cross-section view of an end plate and a liner.

The preferred method of making a plastics (e.g. polypropylene) liner, as depicted in FIG. 4, is vacuum-forming. The liner is vacuum-moulded from sheet polypropylene, in one or more segments as appropriate, creating firstly the general conical form of the liner's reverse surface 18 (complementing the end plate) and secondly the projecting parts 17 in the form of ribs 10 as already described. As seen in FIG. 1 the ribs increase in height towards the centre of the liner. This may be such as to provide a flat rib support contour for the filter layer, but we prefer to maintain a slight conicity as shown.

Vacuum forming of the necessary shapes need not be problematic and routine techniques can be used.

A solid plastics ring 23 providing the annular series of fluid-flow openings 21 is fixed to the inner periphery of the liner 9, e.g by welding.

The filter layer 14,15 can then be secured against the front face of the liner. Suitable filter materials are polymeric materials which can be secured against the tops of the ribs 10 e.g by welding. The filter can also be welded around the perimeter rings of the liner 9.

Examples of suitable filter materials are porous polypropylene sinter and synthetic filter fabrics. These are sophisticated products but their details are known to the skilled person and need not be discussed further here.

A prefabricated assembly of filter layer and liner can be installed against the end plate internal surface and secured in place. The manner of fixing depends on the materials, the end plate construction and the relationship between the end plate and the surrounding column. For example the edge of the assembly may be trapped and clamped between axially-directed faces of the housing wall 16 and a fixed end plate 13, as seen at the bottom of FIG. 4. Trapping may be of the liner only, or of both liner and filter layer.

Where the end plate can move relative to the housing, as at the top of FIG. 4, the outer edge of the liner 9 may be secured only to the end plate. Part of the liner's edge may be folded back around the outward surface of the end plate if desired.

Sealing can be by one or more O-rings 22 as indicated, in line with the skilled person's expertise.

By way of illustration of the surface improvement achieved by this construction, the carefully-machined polypropylene surface of a conventional end-plate has a surface roughness $R_a$ of the order of 50 to 100 μm. By contrast, commercial plastic sheet material such as polypropylene typically has a surface roughness $R_a$ of 2 μm or less and this order of smoothness is not lost on vacuum-forming.

The liner 9 may be made from metal, and some details of this are now discussed.

As regards forming the sheet, the liner (or segment thereof) can be made by inserting a thin flat metal sheet, e.g. of stainless steel, into a suitable press operating against a rigid former having the desired relief pattern geometry. The sheet material is pressed against the former by a counter-surface which is deformable to complement the former and so cause the sheet to conform to its recesses. Such presses are well-known for forming sheet material. The edges are then trimmed as necessary, e.g. by laser trimming t, avoid undesired bending which may occur with mechanical trimming.

FIGS. 1, 2 and 3 show segments 9' of the liner welded into the central conical recess of the metal end plate 1. Welds 11 are made around the perimeter margins of each segment 9'. After welding, electropolishing can be used to reduce surface unevenness e.g. polishing marks and welds.

FIG. 1 illustrates the possibility of providing small channels 7 through the end plate 1, communicating with the region behind each liner segment 9'. The end construction can then be tested for integrity of the welded seals 11 by applying differential gas pressure via the channels 7 to see whether any leakage takes place.

With a metal liner, a metal filter layer is also preferred. A suitable material is a woven steel fiber. Others may be used in line with existing knowledge. Typically a filter disc is produced with a central aperture, a steel ring is welded into the aperture and then held, e.g. by fixing screws, against the central opening of the end plate.

To fix the outer periphery either clamping or welding may be appropriate. FIG. 1 shows a pair of small steps 5 next to the annular securement margin 4 of the end plate 1 which accommodate the thicknesses of the liner 9 and filter layer for substantially flush fitting against the adjacent housing component.

The filter layer may have more than one layer of filter material. A fine-mesh layer may be supported by one or more coarser layers, e.g. at the bottom of the column.

What is claimed is:

1. A chromatography column having an end arrangement comprising an end plate having a fluid flow opening, and a filter extending over an internal surface of the end plate to define a fluid flow zone between them into which the fluid flow opening opens, characterised by a liner having a surface roughness $R_a$ of about 2 microns or less, that between the end plate's internal surface and the filter layer, the liner having a surface relief pattern to space the filter layer from the end plate and maintain the fluid flow zone across the filter.

2. A chromatography column according to claim 1 in which the liner's surface relief pattern comprises an array of spaced ribs each extending away from the fluid flow opening.

3. A chromatography column according to claim 1 in which the liner is of sheet material.

4. A chromatography column according to claim 3 in which the relief pattern is provided by permanent local deformations in the sheet material.

5. A chromatography column according to claim 4 in which the liner is of vacuum-formed plastics sheet or pressed metal sheet.

6. A chromatography column according to claim 1 in which the liner has a conical form complementing a conical form of the end plate's internal surface.

7. A chromatography column according to claim 1 in which the liner's reverse surface is sealingly secured against the end plate's internal surface.

8. A chromatography column according to claim 1 in which the liner is provided as a plurality of segments.

9. A chromatography column according to claim 1 in which the filter layer is secured directly to the liner.

* * * * *